(12) United States Patent
Drost et al.

(10) Patent No.: US 6,538,732 B1
(45) Date of Patent: Mar. 25, 2003

(54) INSPECTION SYSTEM AND METHOD

(75) Inventors: Jeffrey D. Drost, Flanders, NJ (US); David J. Mooney, Flanders, NJ (US); Jon R. Salvati, Skaneateles, NY (US)

(73) Assignee: Everest VIT, Inc., Flanders, NJ (US)

( * ) Notice: Subject to any disclaimer, the term of this patent is extended or adjusted under 35 U.S.C. 154(b) by 0 days.

(21) Appl. No.: 09/564,953

(22) Filed: May 4, 2000

Related U.S. Application Data

(60) Provisional application No. 60/132,400, filed on May 4, 1999.

(51) Int. Cl.$^7$ .......................... G01N 21/00; G03B 17/00
(52) U.S. Cl. ..................................... 356/241.1; 352/243
(58) Field of Search ................. 356/241.1, 241.3, 356/241.4, 241.5; 358/229, 87, 335, 224, 199, 906, 288, 248; 352/243, 293; 248/168, 187, 188.6

(56) References Cited

U.S. PATENT DOCUMENTS

| | | | | |
|---|---|---|---|---|
| 3,730,632 A | | 5/1973 | Chikama | 356/156 |
| 4,115,804 A | | 9/1978 | Morton et al. | 358/107 |
| 4,158,490 A | * | 6/1979 | Gottschalk et al. | 352/243 |
| 4,917,488 A | | 4/1990 | Glass | 356/4 |
| 4,980,763 A | | 12/1990 | Lia | 358/98 |
| 5,065,249 A | * | 11/1991 | Horn et al. | 358/229 |
| 5,070,401 A | | 12/1991 | Salvati et al. | 358/107 |
| 5,552,822 A | | 9/1996 | Nallakrishnan | 348/79 |
| 5,577,130 A | | 11/1996 | Wu | 382/106 |
| 5,867,217 A | | 2/1999 | Okino et al. | 248/358 |
| 6,088,612 A | | 7/2000 | Blair | 600/407 |
| 6,101,408 A | | 8/2000 | Craine et al. | 600/425 |
| 6,293,676 B1 | * | 9/2001 | Holway | 352/243 |

* cited by examiner

*Primary Examiner*—Michael P. Stafira
(74) *Attorney, Agent, or Firm*—Synnestvedt & Lechner LLP

(57) ABSTRACT

A system comprises: (a) an imaging system having an imaging device for transmitting an electrical signal corresponding to an area being imaged, and magnification functionality adapted to magnify the imaged area; (b) a portable support system for supporting the imaging system having a power supply for supplying power to the imaging system, at least one controller for controlling the zooming functionality of the imaging device, and an image output device; and (c) a positioning system for positioning the imaging system independently of the support system; and a method of using the same which comprising: (a) positioning the imaging system independently of the support system such that a target area is in the field of view of said imaging system while at a first magnification level; (b) imaging the area at a second magnification level greater than the first magnification level; and (c) outputting an image of the area.

25 Claims, 10 Drawing Sheets

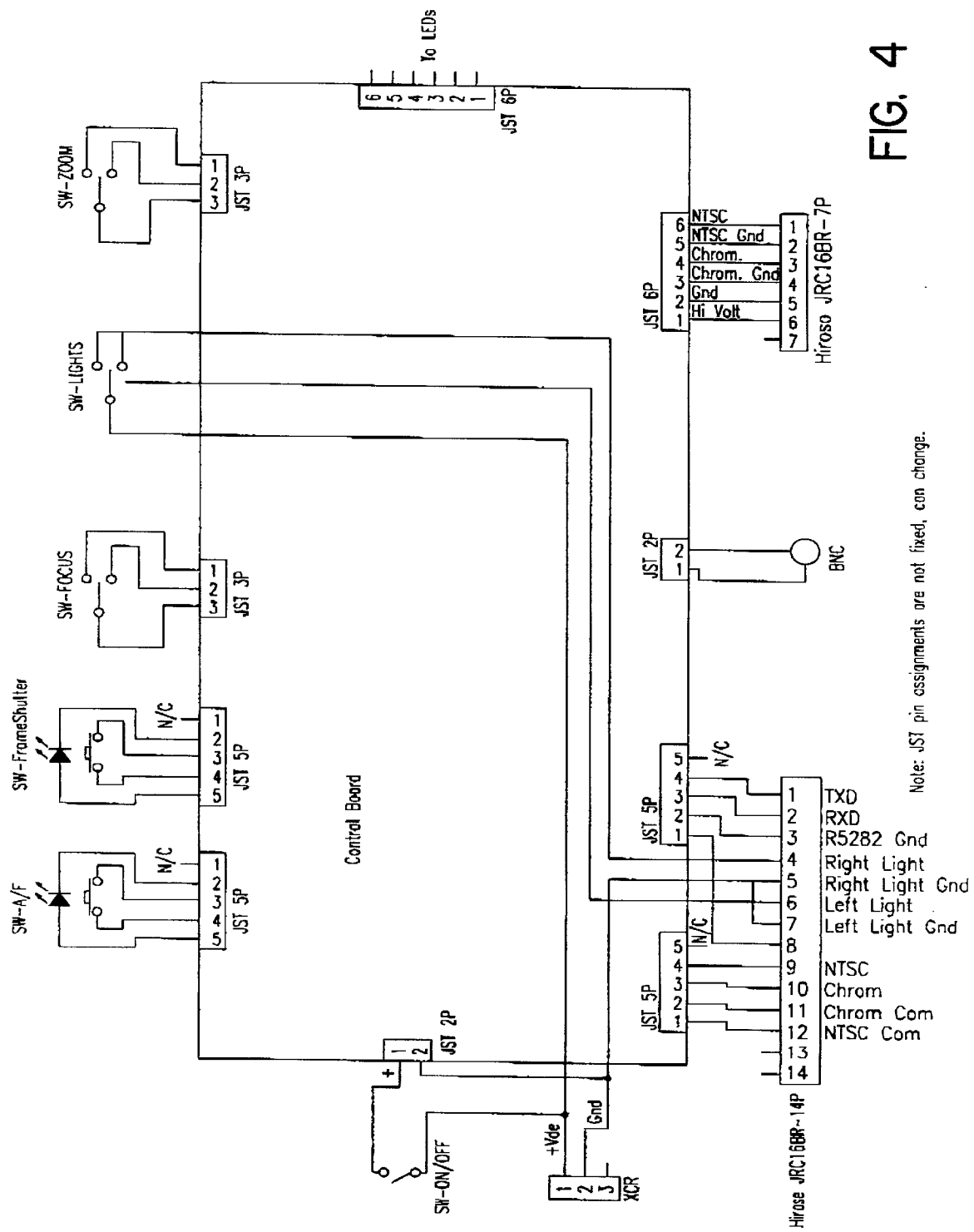

INSPECTION SYSTEM AND METHOD

REFERENCE TO RELATED APPLICATION

This application claims priority to provisional application No. 60/132,400, filed May 4, 1999, which is hereby incorporated by reference.

FIELD OF INVENTION

The present invention relates generally to the inspection of areas which are hard-to-read, inaccessible or uninhabitable for humans. More specifically, the invention relates to the inspection of manholes and the lateral pipes radiating therefrom.

BACKGROUND OF THE INVENTION

It is often necessary to inspect areas under conditions which render them inaccessible or otherwise uninhabitable by humans over an extended period. These conditions include, for example, small confined spaces, lack of air/oxygen, presence of toxins, radioactivity, contamination, excessive dust, dirt and filth, and high noise levels. These conditions can be found in areas common to storm and sewer pipes, nuclear reactors and containments, fossil fuel plants and petrochemical refining facilities just to name a few. Although the need for inspection and the problems associated with these areas varies, the inconvenient and time-consuming nature of performing the inspection remains a constant.

For illustrative purposes the inspection of storm and sewer pipes is considered in detail, although the scope of the present inventor is by no means limited to this application. Most municipalities contain a vast network of storm and sewer pipes which often represent the oldest infrastructure in the community. Periodically, these pipes must be inspected for problems such as cracks, blockage, build-up, and root infiltration. If a problem is detected, detailed images must be obtained pursuant to formulating a plan to remedy the situation. To this end, it is common for an invasive device such as a pipe crawler or push camera to be introduced into the pipe to perform the inspection and, at the same time, to obtain details of any problem encountered.

Although effective in obtaining detailed images, using a pipe crawler is inconvenient and requires a great deal of time to set up and operate even if no problem is discovered. In other words, the pipe crawler obtains detailed information regardless of whether a problem exists. Thus, the conventional approach tends to be superfluous in most cases. In addition to being superfluous, pipe crawlers frequently are limited by the pipes they physically can enter and require a great deal of control circuitry which adds cost and complexity to the inspection process.

Therefore, there is a need for a more convenient approach to inspect underground pipes without the time and complexity of using a pipe crawler or push camera. The present invention fulfills this need among others.

SUMMARY OF INVENTION

The present invention provides for a quick and convenient approach to ascertain the condition of an inaccessible or uninhabitable area before initiating a more comprehensive inspection. More specifically, rather than physically entering the area to be inspected with a robotic or push camera, a self-contained, highly-maneuverable, hand-held inspection system is positioned with the area in its field of view and then is zoomed in to obtain an image at the desired magnification. Thus, the device obtains images of inaccessible or uninhabitable areas by maneuvering an imaging device and using its magnification capabilities rather than by physically entering the area.

Once the images are obtained, an analysis may be performed to determine whether problems such as cracks, blockage, and root infiltration exist. The images obtained preferably are in a readily-transmitted form, such as a bit-map, thereby allowing them to be transmitted for off-site analysis if need be. If no problem is detected, then the device can be moved quickly to another area to perform another inspection. On the other hand, if a problem is detected, a pipe crawler or other invasive type of inspection may be performed to obtain the details necessary to remedy the situation. This way, the time of setting up and operating a pipe crawler or similar device is not wasted on areas that are in acceptable condition.

To facilitate the inspection approach described above, several attributes of an inspection system have been identified. First, the device should be capable of performing an inspection both close up and from a distance, and, thus, should have a relatively-high magnification ratio and a tolerance to low-light conditions. Second, the inspection system should be self-contained. To this end, its power supply, operator's control, and monitoring/recording should be portable, preferably, carried on the user performing the inspection. Being self-contained, the device is not encumbered with power cords or control leads. Third, the device should be highly maneuverable to position it such that the subject matter is in its field of view. Properties that add to maneuverability include, for example, light weight, conveniently situated controls, and means for positioning the imaging portion of the device. An extended boom, for example, allows the device to be inserted into difficult-to-reach areas. Fourth, the images obtained should be readily available for review and analysis to determine whether a more comprehensive inspection is warranted. Preferably, a digital framegrabber is used to transform the image into a readily-transmitted medium, which, for example, can be transmitted via e-mail anywhere in the world for off-site analysis. Fifth, the device should be durable to withstand harsh environments and rugged use. The preferred device thus has no external wiring and is sealed to render it waterproof.

Accordingly, one aspect of the invention is a system having one or more of the above-referenced attributes for performing an inspection as described above. In a preferred embodiment, the system comprises: (a) an imaging system having an imaging device for transmitting an electrical signal corresponding to an area being imaged, and magnification functionality adapted to magnify the imaged area; (b) a portable support system for providing functional support to the imaging system and having a power supply for supplying power to the imaging system, a controller for controlling the magnification functionality of the imaging device, and an image output device for outputting the image based on the electrical signal; and (c) a positioning system connected to the imaging system and adapted for moving the imaging system independently of the support system.

Another aspect of the invention is a method of using the inspection system for performing an initial inspection of an area where close up inspection is undesirable, inconvenient or impractical. In a preferred embodiment, the inspection comprises: (a) positioning the imaging system described above independently of the support system such that the field of view of the imaging system contains the area to be imaged while at a first magnification level; (b) imaging the area at a second magnification level greater than the first magnification level; and (c) outputting an image of the area.

The method of the present invention is particularly applicable to inspecting sewer and storm pipes which are accessible through a manhole; In a preferred embodiment, inspecting storm and sewer comprises: (a) extending an imaging system into a manhole; (b) imaging the interior of the manhole at a first magnification level; (c) locating a lateral pipe connected to the manhole; and (d) imaging the interior of the lateral pipe at a second magnification level greater than the first level.

BRIEF DESCRIPTION OF THE DRAWINGS

FIG. 4 shows a layout diagram of the circuit board of the operator's control of FIG. 3;

DETAILED DESCRIPTION OF PREFERRED EMBODIMENT

Figure 1:
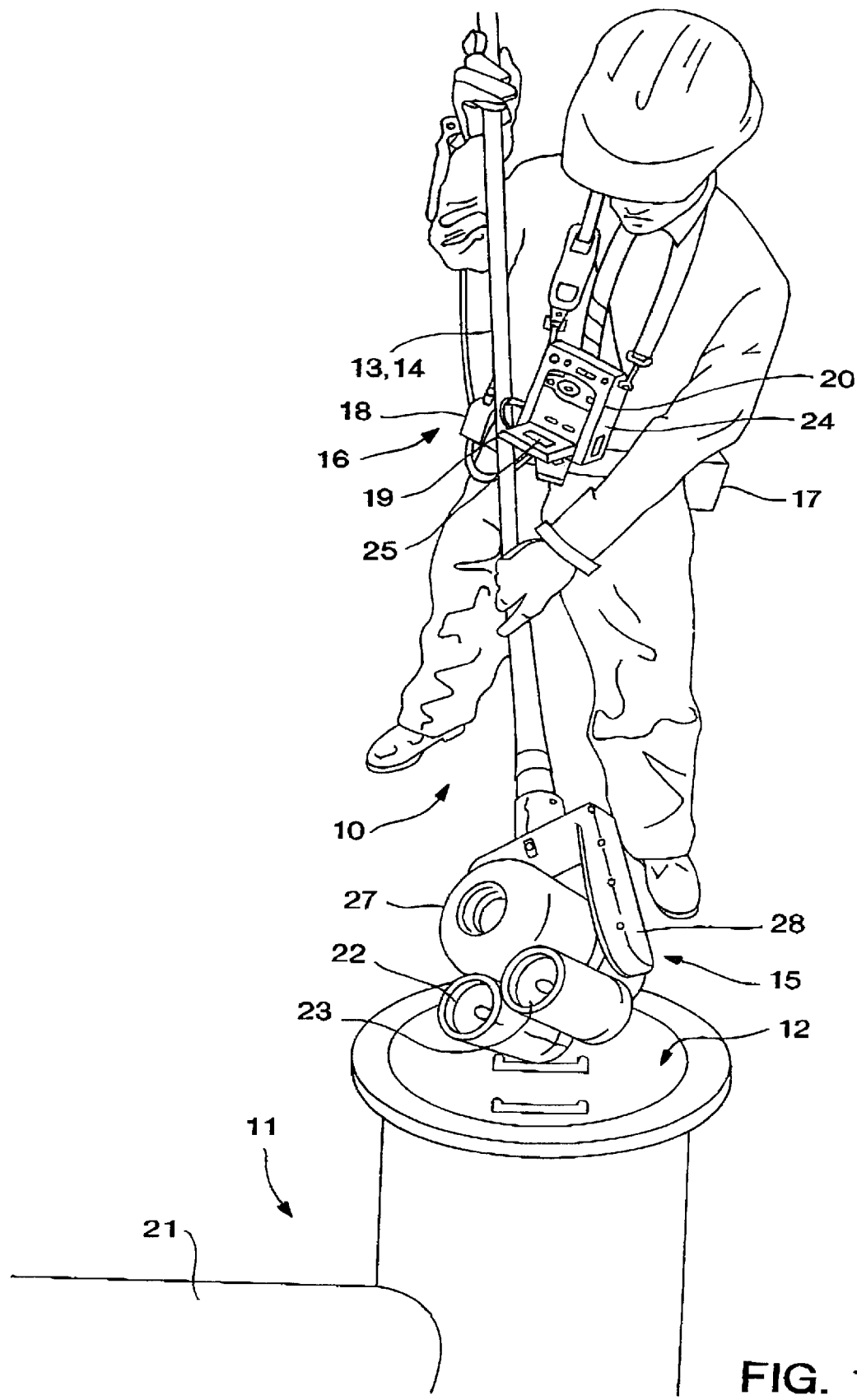
FIG. 1 shows a user inserting a preferred embodiment of the device into a manhole.

Referring to the drawings, FIG. 1 shows a user inspecting a storm or sewer pipe using a preferred embodiment of the inspection system 10 to ascertain whether a more comprehensive inspection is warranted. More specifically, using a positioning system 13, which, in this embodiment is a telescoping boom 14, the user lowers the imaging system 15 into a manhole 12. The user is wearing a support system 16 which in this embodiment comprises a power supply 17 and control functionality 18 worn on a belt 19, and monitoring and recording functionality 20 worn around the users neck. A detailed illustration of the belt 19 is provided in FIG. 1a. The components of the support system are described in greater with respect to FIGS. 2–5.

While observing a monitor 25, the user inserts the image system into the manhole 12. Imaging the interior of the manhole typically is performed in close proximity thereto A and thus at a low magnification level which provides a wide field of view. The user then would inspect the manhole's condition and attempt to locate the penetration of a lateral pipe 21 in the manhole 12. It may be preferable to illuminate the interior of the manhole using a flood light 22 which provides a wash of light commensurate with the wide field of view. Once the entrance to the lateral pipe 21 is located, the user positions the imaging system 15 with the interior of the lateral pipe 21 in its field of view. To obtain images further down the pipe, the user increases the magnification level via the control functionality 18. It may be preferable to illuminate the viewed area using a spot light 23 which provides a high intensity, relatively-focused light commensurate with the relatively narrow field of view associated with high-magnification.

Next, images of the interior of the lateral pipe may be recorded. In this embodiment, a digital image is recorded with a framegrabber 24. The digital images then are available for on-site analysis or may be transmitted over a telecommunicative link for analysis by others off-site. Accordingly, the preferred embodiment of the present invention enables a user to obtain quickly and conveniently digital images of lateral pipes which can be readily transmitted for analysis by others. If a problem is detected, a more comprehensive inspection may be conducted.

Although FIG. 1 depicts the inspection of a pipe through a manhole, it should be understood that the present invention is applicable to the inspection of any area located in an inaccessible and/or uninhabitable location as described above. For example, the device may be used to quickly and conveniently inspect the containment of a nuclear reactor without erecting scaffolding. By performing inspections quickly without extensive set-up, the overall radiation dose incurred by personnel is reduced. Additionally, in addition to nuclear reactors, the inspection system of the present invention can be used in a host of other applications including, for example, the inspection of snubbers, pipe hangers, pipe insulation, storage vessels, and the like which are commonly found in power generating stations (such as fossil fuel, nuclear, and hydro), refineries, and, practically speaking, any other significant industrial facility.

Figure 2:
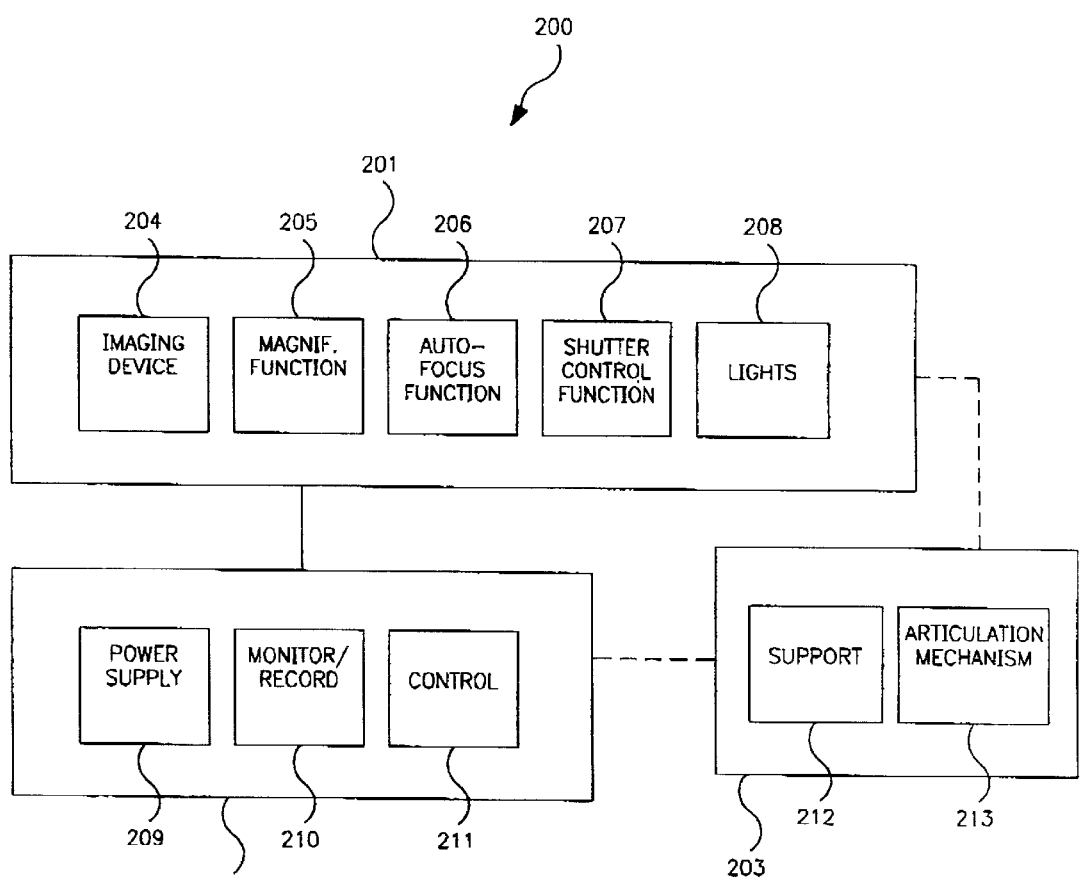
FIG. 2 shows a schematic of the system.

Now referring to FIG. 2, the subsystems of the inspection system will be described in greater detail. For illustrative purposes, the system 200 may be divided into three subsystems: (1) the imaging system 201, (2) the support system 202, (3) the positioning system 203 and optionally (4) the measuring system 214. It should be understood, however, that the division of the system into three components is for illustrative purposes and should not be construed to limit the scope of the invention. Indeed, the various systems may be further divided into subsystems, or their various components and functions may be combined and integrated.

1. Imaging System

The function of the imaging system 201 is to generate and transmit an electrical signal corresponding to an area being imaged. The heart of the imaging system is an imaging device 204 which translates an image to an electrical signal. The imaging device 204 may be any conventional or subsequently-developed device for imaging a target object. The term "imaging" broadly refers to a characterization or representation of the target object based on a particular property, such as, for example, its tendency to reflect or absorb electromagnetic radiation, its thermal profile, or its acoustical profile. Devices for imaging these characteristics or properties are known and include, for example, video cameras, still cameras, digital cameras, infrared detectors, X-ray machines, lasers, microphones, sonic or ultrasonic transducers, radar, and the like.

In the preferred embodiment, the imaging device 204 provides a video image of the target area. More preferable, the imaging device comprises a charge coupled device (CCD) which is well known in the art. The CCD electronically captures an image of the video field in an analog format and the analog information is relayed to the monitor/digital recording functionality 210 of the support system 202. Preferably, the CCD is a low lux CCD having a sensitivity of at least 6 Lux at f1.4, and, more preferable at least 3 Lux at f1.4.

The imaging system 201 also includes a lens system/magnification functionality 205 which has inherent optical characteristics such as distortion, focal length, and field of view, some of which are used in the calculation of the target size as is described in detail below. The preferred lens characteristics of the imaging system include a focal length of about 4 mm to about 74 mm, a field of view of about 2.7° to about 48°, and a minimum focal distance of about 10 mm to about 800 mm. The lens system/magnification functionality comprises a series of lenses that interact to change the focus and magnification. As is known in the art, the system includes motors that manipulate the positioning of the various individual lenses in relation to each other and in relation to the CCD in order to effect different foci and magnification configurations.

The lens system/magnification functionality 205 should contain magnification functionality with a relatively high magnification ratio. More specifically, the intended applications of the inspection system of the present invention usually requires a panoramic, wide angle view for general viewing, and a magnified view for details. Again, such functionality is well known in the art and may comprise, for example, optical magnification or electronic magnification using techniques such as pixel enlargement or interpolation. In a preferred embodiment, the magnification functionality has a magnification ratio of no less than about 6:1, more preferably, no less than about 12:1, and even more preferable, no less than about 50:1. In a highly preferred embodiment, the magnification ratio is 72:1 and is the composite of an 18:1 optical zoom and a 4:1 digital zoom.

The imaging system preferably comprises autofocusing functionality 206. Again, autofocusing is known in the art. More preferably, the imaging system provides for manual focusing thereby allowing the user to control the focus if, for example, the autofocus is focusing on the wrong object.

In a preferred embodiment, the imaging system also enables the user to control the shutter speed manually through shutter control functionality 207. More specifically, in certain applications, for example, in low light conditions, it may be desirable for the user to extend the exposure time to increase the amount of light in the image. For example, shutter speed may be increased from a typical period of about 1/50 second to about 1/3 second.

Suitable imaging system having the above-mentioned magnification and functionality are commercially available from, for example, Sony Company (Model No. FCB-IX47).

In the preferred embodiment, the imaging device and the above-mentioned functionality are integrally packaged. Furthermore, this package may be enclosed within an enclosure, as discrete units, or its structure may be integral to the enclosure. Preferably, the enclosure is splash proof. More preferable, the enclosure is sealed and watertight thereby allowing it to be submerged. To this end, it may be desirable to pressurize the enclosure to match the anticipated hydrostatic pressure to minimize the risk of leakage.

In a preferred embodiment, the imaging system comprises one or more lights 208 to illuminate the target area and improve the quality of the images obtained. Given the relatively high magnification ratios of the imaging system, it is preferable to provide at least two types of lights, a flood light and a spot light. The function of these lights is well known in the art. Specifically, a flood light is useful for illuminating a relatively close, broad area, while a spot light illuminates a focused area at a further distance. The lights may be packaged individually or in combination, and may be integral with the imaging device or separate therefrom.

2. Support System

Figure 1A:
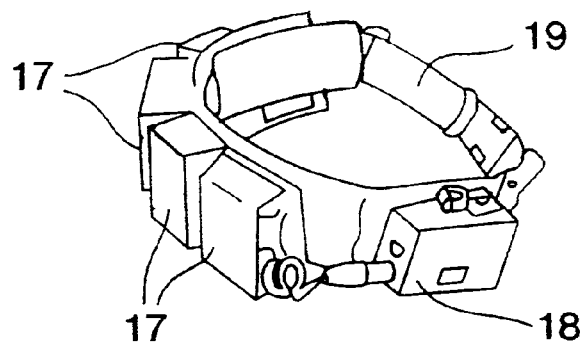
FIG. 1a shows the belt of the preferred embodiment of FIG. 1.
Figure 1B:
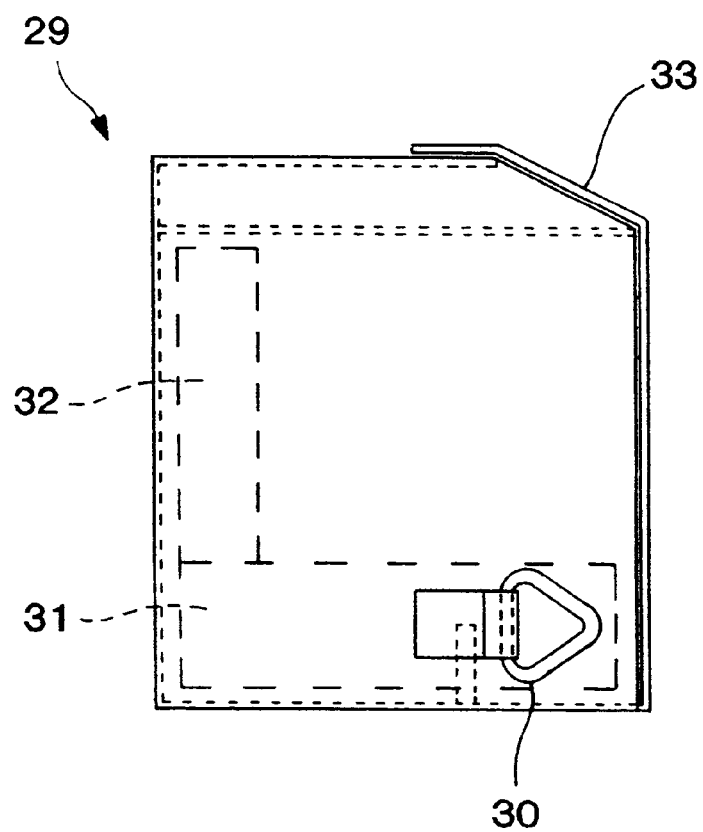
FIG. 1b shows a bag for supporting the monitor/recording device of FIG. 1.

The support system 202 is a portable system and functions to power and control the imaging system. To this end, a preferred support system comprises a power supply 209, operator's control 211, and monitoring/recording functionality 210. In a preferred embodiment, the power supply and operator's control are mounted on a belt 19 as shown in FIG. 1a adapted to be worn by the user. Likewise, the monitor/recording functionality preferably is supported by a bag 29 as shown in FIG. 1b adapted to be worn around the user's shoulders/neck. The bag 29 preferably has a hook & loop fastened flap 33 and is configured to support a recording device 31 and a monitor 32 (shown in dotted lines).

The operator's control 18 is used to control the on/off operation of the imaging device as well as the other functions such as magnification, manual focus and shutter speed. In a preferred embodiment, this control functionality is integrated into a single enclosure as shown in FIGS. 3a–e. This figure shows five sides of a housing which is adapted to be mounted to the belt 19 as shown in FIG. 1a.

Figure 3B:
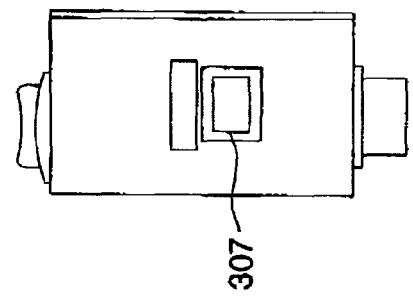
FIGS. 3a–e show the operator's control in the preferred embodiment of FIG. 1.
Figure 3A:
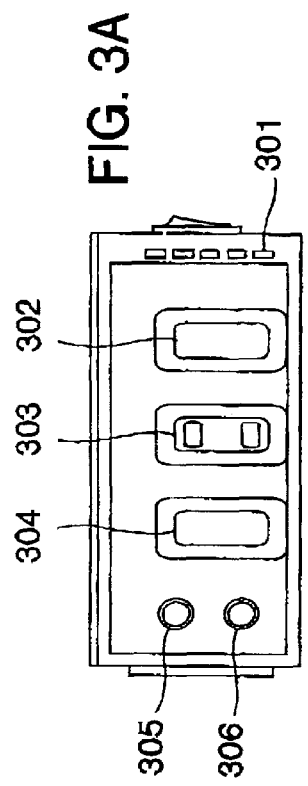
Figure 3E:
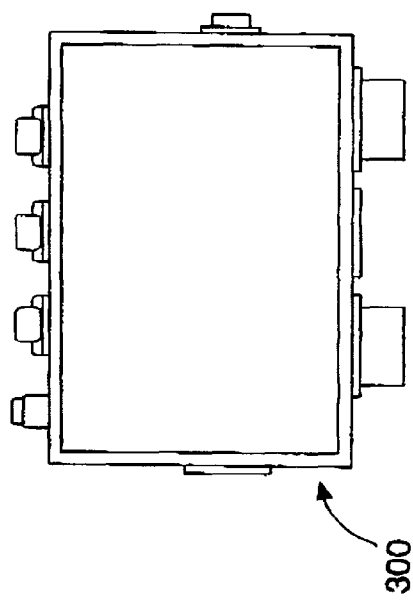

FIG. 3a is a top view of the housing and shows the following controls: a series of LEDs 301 which are used to provide an indication of battery life; a momentary-on rocker switch 302 for adjusting the magnification from wide angle to telescopic; a three-position rocker switch 303 with LEDs indicator lights for light control such that when one side is depressed the flood light is on, when the other side is depressed the spot light is on, and when in the middle, both lights are off; a momentary-on rocker switch 304 the operator uses to send signals to the focus and zoom motors in order to change the positioning of the lenses in the lens system 205 for optimum viewing. Preferably, the focus and zoom motors contain servo-feedback mechanisms which provide information to a microprocessor (discussed below); a manual/autofocus selector knob 305 with an LED indicator; and a shutter speed control knob 306 with an LED indicator.

Figure 3D:
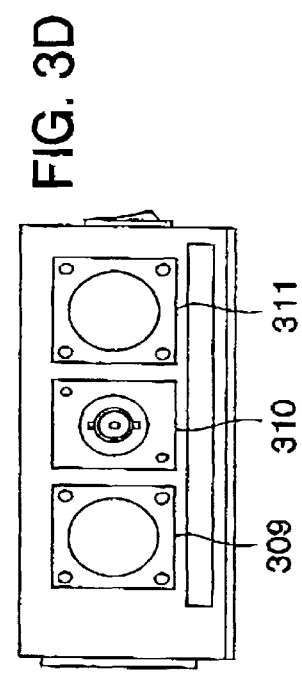
Figure 3C:
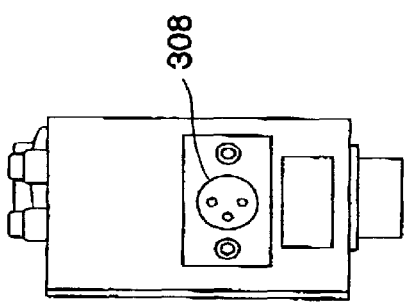
Figure 5A:
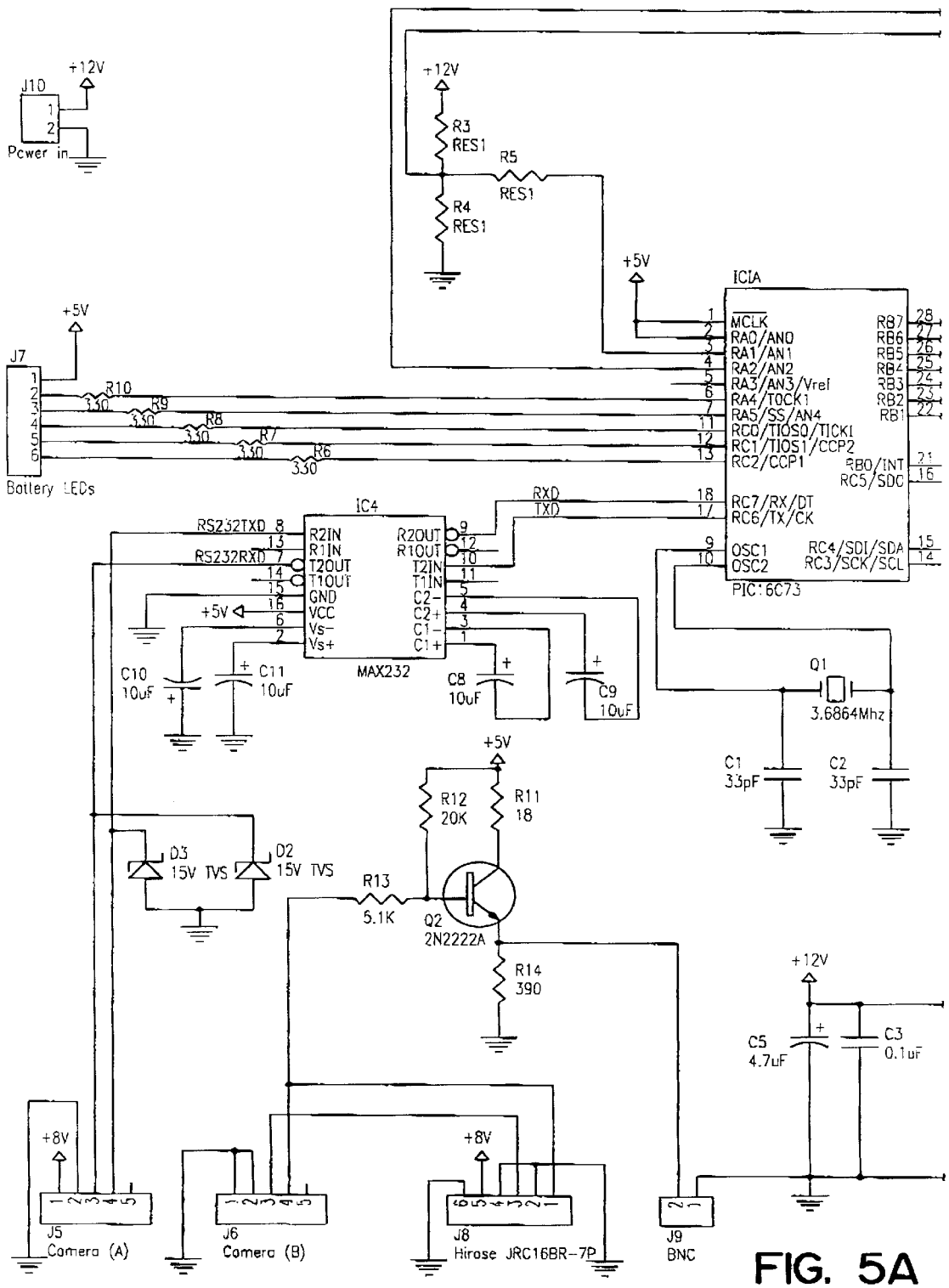
FIG. 5 shows a detailed schematic diagram of the circuit board of FIG. 4.
Figure 5B:
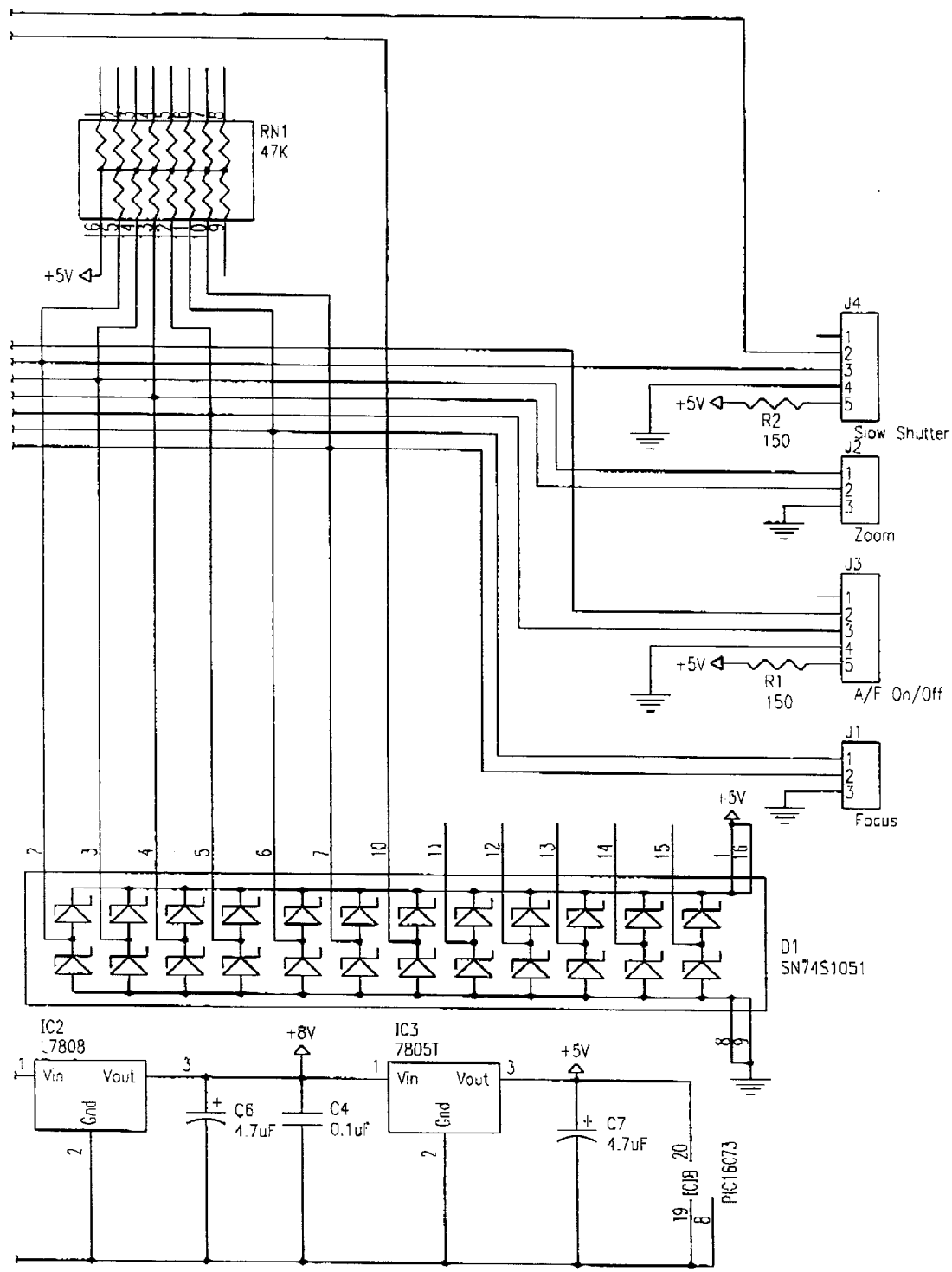

FIG. 3b is a side view of the control housing and shows a main on/off switch 307 for turning the imaging system on and off. FIG. 3c is the other side view and shows the power input 308 to supply power to the various control functionality. FIG. 3d is a bottom view of the control housing and shows: an input 309 for the video signal from the imaging system; a video output 310 to the monitor/framegrabber (described below); and an optional output 311 for remote monitoring or recording.

FIG. 4 shows a layout diagram of a preferred embodiment of a circuit board housed within the control housing of FIGS. 3a–e. As shown, the circuit board interfaces the various control functionality and transmits commands to and receives acknowledgments from the imaging system. In a preferred embodiment, the circuit board comprises a programmable controller (IC1A) as shown in the circuit board's schematic in FIG. 5. The programmable controller provides for a configurable control functionality where the function of the switches described above may be reconfigured through a simple software change. Although the control functionality may be hardwired directly to the imaging system, interfacing the imaging system through a circuit board having a programmable controller is preferred from a flexibility standpoint. Additionally, the communication link between the control functionality and the imaging system may be metallic or wireless, although metallic is preferred.

Referring back to FIG. 2, the output device 210 preferably comprises a monitor which allows the user to view the images being transmitted by the imaging system in real time. Such a function is highly preferred as it provides feedback to the user as he or she positions the imaging system. Monitoring devices are well known in the art. In the preferred embodiment, the imaging system is lightweight and supported in such a way as to allow the user to view it conveniently while operating the positioning system. More preferably, the monitor is worn around the user's neck as shown in FIG. 1. Still more preferably, the monitor is contained in a bag or similar device to provide shielding from the sun to improve view ability and reduce glare.

In the preferred embodiment, the output device 210 comprises a recording device for recording one or more images for evaluation later. Preferably, the recording device is a digital framegrabber. The framegrabber is adapted to convert an analog signal to a digital image and conveniently store the image on a computer-readable medium such as a disk. Images may be stored, for example, in JPEG or a bit-map format which is readily-transmitted over conventional telecommunicative links anywhere in the world without loss of resolution. It has been found that having images in such a readily-transmittable form provides others, who need not be on site, with the opportunity to analyze the images and determine whether a more comprehensive inspection is required while personnel are on site and in position to perform such a comprehensive inspection.

In a preferred embodiment, the monitor and framegrabber are integrated into a single unit to provide for a conveniently transportable package. Suitable monitor/framegrabbers are commercially available from, for example, Sony Company (Model No. MVC-FDR3).

Alternatively or additionally, another type of recording device may be used. For example, it may be preferable under certain circumstances to use a video tape recorder. Suitable monitor/tape recorders are commercially available from, for example, Sony Company (Model No. GV-D900).

The power supply 209 supplies power to the imaging system and to other components of the support system requiring power. Preferably, the power is supplied by one or more rechargeable batteries releasably mounted to the belt 19 as shown in FIG. 1. Given the weight of batteries, particularly wet cells, it may be preferable under some circumstances to place one or more batteries on the ground during operation of the inspection system. Although rechargeable belt-mounted batteries are preferred, power may be provided through other conventional means such as a portable generator.

3. Positioning System

The position system 203 functions to position the imaging device to image the desired area. Since the inspection system of the present invention is intended to inspect hard-to-reach areas or areas which are generally inaccessible to humans, it is preferable for the inspection system to be highly maneuverable. In a preferred embodiment, the positioning system comprises a support 212, more preferably an elongated member, which has the housing of the imaging system mounted on one thereof. With such a configuration, a user can insert the end containing the imaging system into, for example, a pipe, and manipulate it to position the imaging system such that the target area is in its field of view. In a more preferred embodiment, the elongated member is a telescoping boom 14 as shown in FIG. 1.

Preferably, the positioning system comprises an articulated mechanism 213 interposed between the housing of the imaging system and the boom to allow the imaging system to move relative to the boom. This articulated mechanism preferably is a trunnion assembly 28 assembly having an axis perpendicular to the axis of the boom as shown in FIG. 1. A simple trunnion is preferred because it provides for independent movement of the imaging device without incurring the cost, weight and complexity of a traditional pan and tilt mechanism, although such mechanisms are nevertheless within the scope of the invention.

In a preferred embodiment, the imaging system is detachable from the positioning system to allow for its stationary operation. Such a configuration may be preferred, for example, in a surveillance application.

4. Measurement System

Figure 6:
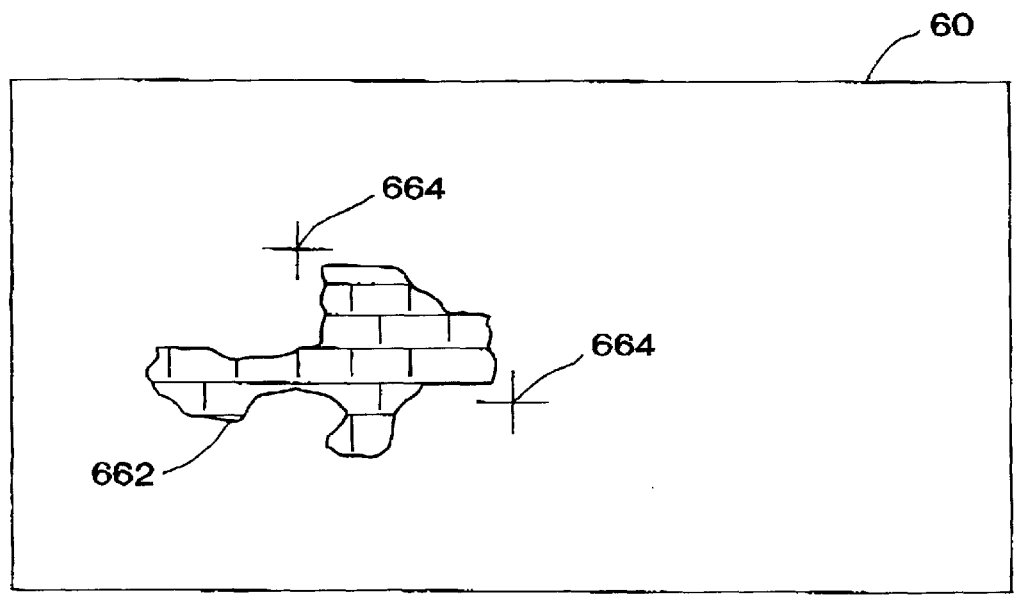
FIG. 6 is a front view of a keypad.
Figure 7:
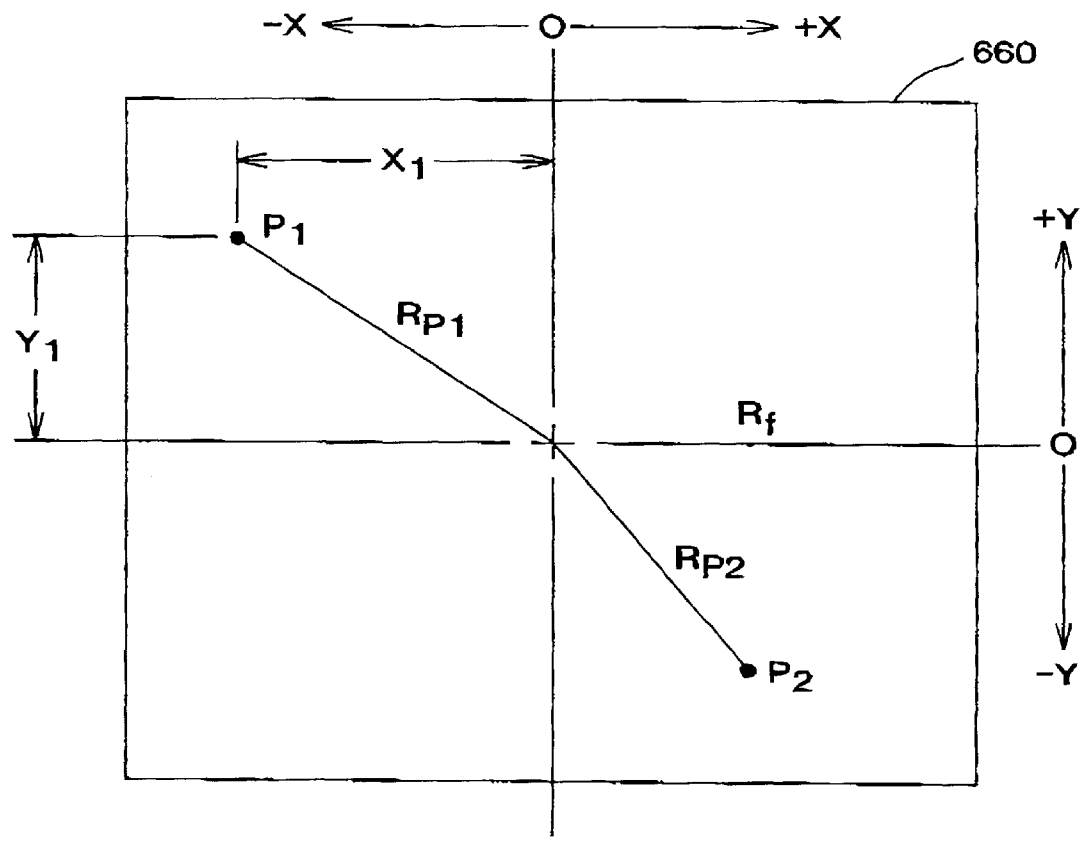
FIG. 7 is a front view of a video screen.

The measuring system functions to provide the user with a measurement of a selected object in the field of view. More specifically, referring now to FIG. 6, a monitor 660 is depicted which displays the video field, including the target object 662 which is to be measured. The monitor is part of the output device 210 as described above. As is known in the art, the monitor 660, or video monitor, comprises a number of pixels. The system includes a video overlay generator 654 (FIG. 3), which generates an information display which overlays the video image. The information display includes measurement cursors 664–664 which are manipulated by the user and are used to mark the target object 662 to be measured, as depicted in FIG. 6. Referring now to FIG. 7, the measurement cursors 764 are controlled by the operator and in the preferred embodiment the operator uses a keypad 770 to control the movements of the cursors. Of course, other means to move and mark the cursor positions are known to those skilled in the art, such as a computer mouse. The keypad 770 preferably is part of the operator's control 211. The keypad 770 includes four cursor positioning keys 772 that move the cursors on the screen in the horizontal and vertical planes. The keypad 770 includes a cursor marking key 774 which, when depressed by the operator, marks the position of the cursor 664 on the screen at one end of the target object 662. The operator then moves the cursor 664 to another point on the screen at the other end of the target object 662. When the second point on the screen has been reached, the cursor marking key 774 is again depressed, and that point is also marked on the screen. In this manner, the operator places marks at the periphery of the target object 662 as it appears on the screen 660. The distance in pixels between the marks is used in the calculation of the size of the target object 662, as explained below in more detail.

Figure 8:
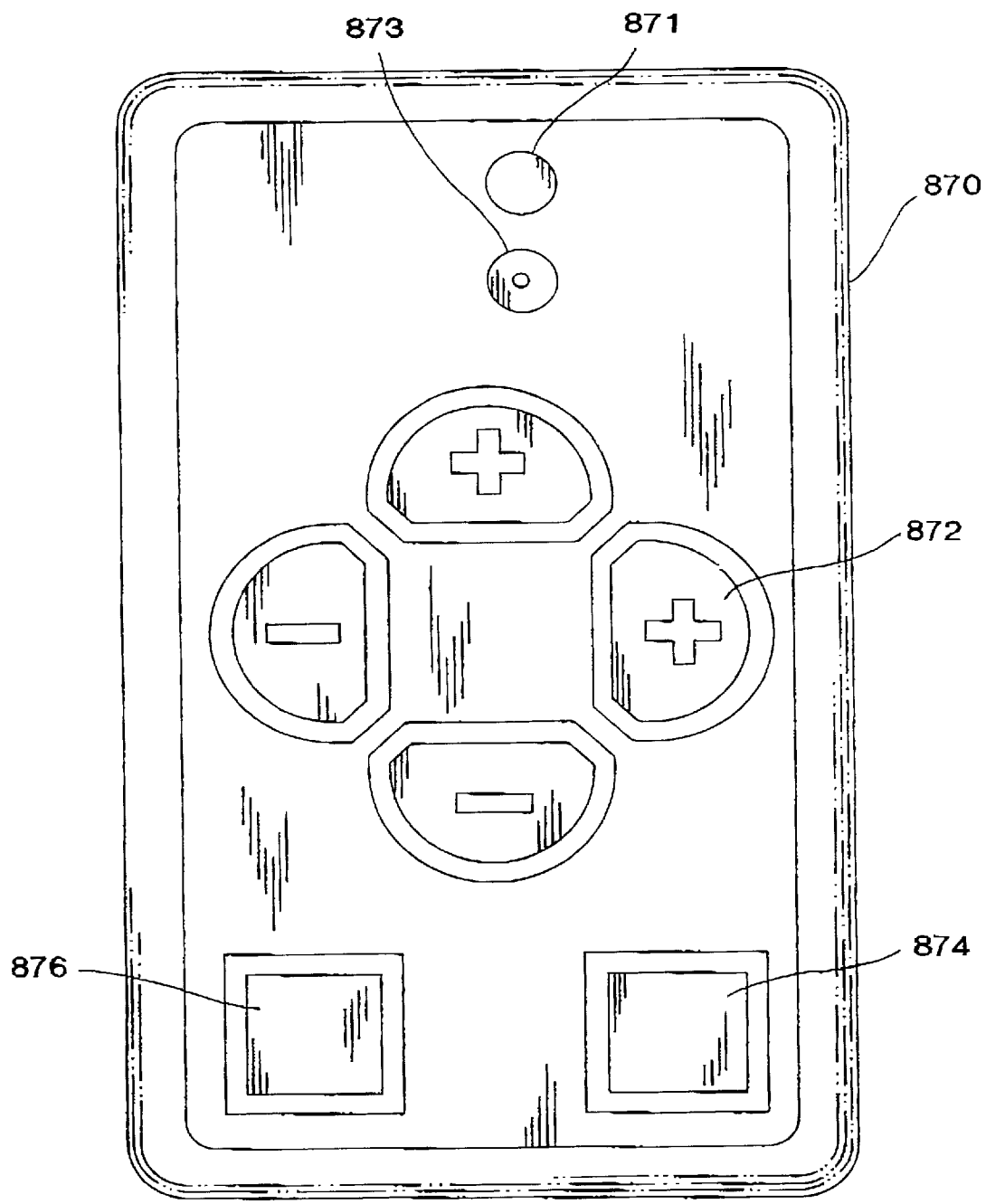
FIG. 8 is a front view of a video screen with a graphical overlay.

In order to determine the size of an object, the first step is to determine the optical distortion correction of a point of the lens system at a given magnification, and preferably for each of calculation, the magnification at M=1× is determined. Referring now to FIG. 8, there is depicted a screen 860 made up of a number of pixels with a graphical representation overlaid to show how the optical distortion correction of a point is used to determine the distance between two points. For simplicity of explanation, the pixels that are depicted have a ratio of 1:1, as opposed to the standard NTSC ratio of 4:3. One skilled in the art would recognize the appropriate mathematical manipulation required to covert between the ratios. The lens system has a known distortion fraction at the flat of square. The optical distortion correction of a point $C_{P1}$ is determined by the formula:

$$Cp_1 = \frac{1}{1+D_1} = \frac{1}{1 + \frac{D(R_{P_1})^2}{R_f^2}}$$

$$Cp_1 = \frac{1}{\frac{1 + D((X_1^2 + Y_1^2)^5)^2}{R_f^2}}$$

where
 Rf=Radius to Flat
 Rp=Radius to Point
 $D_1$=Distortion fraction at Point
 D=Distortion fraction at flat of square
 $CP_1$=Correction factor for distortion unmapping of $P_1$.

After the optical distortion correction factor is determined for a point, the value of the coordinates at any two particular points can be determined by:

$X_{1_c}$=Distortion Corrected=$CP_1X_1$
$Y_{1_c}$=Distortion Corrected=$Cp_1Y_1$
$X_{2_c}$=Distortion Corrected=$Cp_1X_2$
$Y_{2_c}$=Distortion Corrected=$Cp_1Y_2$ Knowing the distortion corrected values, the distance Pn between points $P_1(X_1Y_1)$ and $P_2(X_2Y_2)$ is determined by $$Pn=((X_{1_c}-X_{2_c})^2+(Y_{1_c}-Y_{2_c})^2)^{0.5}$$

Knowing the value of Pn at magnification M=1, the size of a target object on the video screen after the operator has brought the object into view and focused is 5 determined by:

$$\text{Object Size}=M*K*Pn$$

Where K is a constant

The constant K is determined by using the known characteristics of the lens. The constant K will vary depending upon the type of lens and imager used, but once the characteristics are determined for a particular lens and imager, the number is a constant. The constant K may also contain the conversion math for the measurement system, i.e. inches, centimeter, or millimeters. The calculation of K is determined using the following formula:

$$K = \frac{1}{(\#\text{ of pixels})*L}$$

where L is determined by:

$$L = \frac{\left(\frac{1}{(1-V)}\right)}{2*OD*\text{TAN}\left(\frac{FOV}{2}\right)}$$

where

V=the percent distortion across horizontal axis of lens
OD=Object Distance
FOV=Field of View (across an axis, preferably the horizontal axis)

Figure 9:
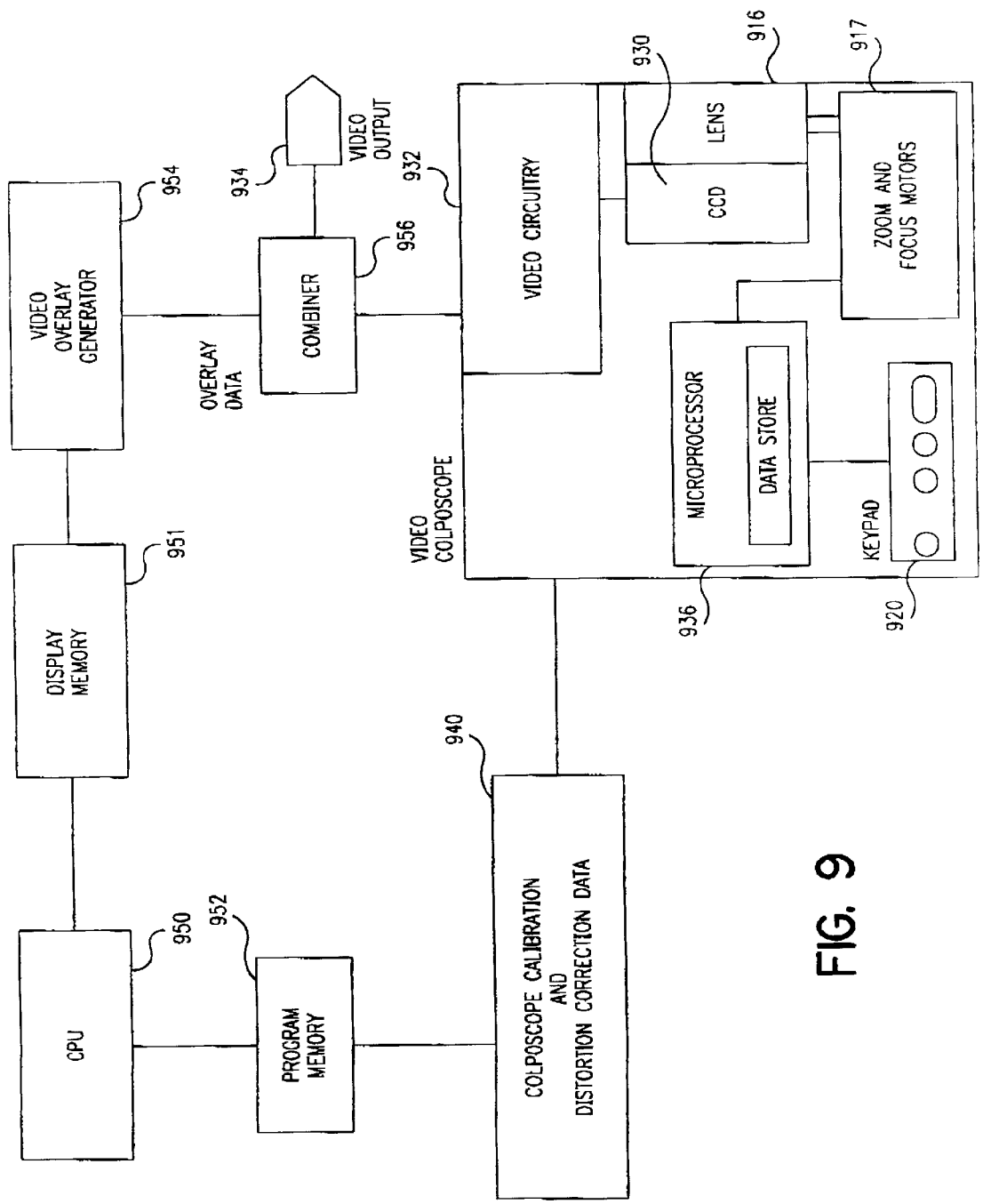
FIG. 9 is a block diagram of the imaging system.

In use, the imaging system is positioned to provide an adequate view of the target area 662. Referring to FIG. 9, the imaging system 910 is automatically calibrated 40 when powered up, which includes the distortion correction data and also includes the focus and magnification motors being zeroed. The target object 662 is brought into the preferred viewing configuration on the screen 660 by the operator using the focus 821 and zoom buttons 822. The exact object distance (OD) is determined by feedback from the focus motor 917 and calculating the deviation from zero. The magnification factor M is determined by the position of the zoom and focus motor 917 servo-feedbacks and is stored in data storage/microprocessor 936. The CCD 930 relays the video information to the video circuitry 932, which then relays the video information to the video output 934 via a combiner 956. The video display information is also stored in display memory 951. The video overlay generator 954 is activated by the operator manipulating the keypad 870 (FIG. 8) by depressing the measurement key 871, which causes the generation of the on-screen cursor 864. The operator manipulates the cursor 664 to mark the periphery of the object 662 using the cursor keys 872 and the marking key 874. After the operator has marked the periphery of the object, the operator depresses the measuring key 876 which causes the overlay data from the combiner 956 to be forwarded to the CPU 950. The size of the object is determined using the calculation algorithms which are stored in program memory 952. The operator returns the imaging system to non-measurement mode by depressing the imaging system key 873.

Of course, in addition to the linear size of an object, the area of an object can be also be calculated. For example, the area of a generally square shaped object could be determined by marking the four corners of the object, determining the distance between the four corners using the method discussed above, and then applying the appropriate geometrical formula.

While the present invention has been particularly shown and described with reference to the preferred mode as illustrated in the drawing, it will be understood by one skilled in the art that various changes in detail may be effected therein without departing from the spirit and scope of the invention as defined by the claims.

What is claimed is:
1. A system of inspecting comprising:
an imaging system having an adjustable field of view and comprising at least:
an imaging device for transmitting an electrical signal corresponding to an area within said field of view:
a lens system having/magnification functionality to magnify the imaged area, said lens system/magnification functionality having a magnification ratio of no less than 50; and
a waterproof enclosure containing said imaging device and said lens system;
a portable support system operatively connected to said imaging system and adapted to provide functional support to said imaging system, said portable support system comprising at least:
a power supply for supplying power to said imaging system
at least one controller for controlling said imaging system;
an image output device for outputting an image based on said electrical signal; and
an elongated member positioning system connected to said imaging system and adapted for moving said imaging system independently of said support system.
2. The inspection system of claim 1, wherein said magnification functionality has a magnification ratio of is no less than about 70:1.
3. The inspection system of claim 1, wherein said imaging system comprises at least one flood light and at least one spot light.
4. The inspection system of claim 1, wherein said support system is adapted to be worn by a user.
5. The inspection system of claim 1, wherein said portable power supply comprises a rechargeable battery.
6. The inspection system of claim 1, wherein said image output device comprises a digital framegrabber.
7. The inspection system of claim 1, wherein said image output device comprises a monitor for viewing video.
8. The inspection system of claim 7, wherein said monitor is contained with a bag having a strap adapted to be worn around the neck a user.
9. The inspection system of claim 1, wherein said image output device comprises a video recorder.
10. The inspection system of claim 1, wherein control for said magnification functionality is mounted to a belt adapted to be worn by a user.
11. The inspection system of claim 1, wherein said power supply comprises a battery proximate to a user.
12. The inspection system of claim 1, wherein said positioning system comprises a boom upon one end of which said imaging system is mounted.

13. The inspection system of claim 12, wherein said boom comprises telescoping members.

14. The inspection system of claim 12, wherein said position system comprises a trunnion assembly disposed between said imaging system and said boom thereby allowing for the movement of said imaging system relative to said boom.

15. The inspection system of claim 1, further comprising a measurement system adapted for calculating the size of an object in the field of view of said imaging system.

16. A system of inspecting comprising:
an imaging system having an adjustable field of view and comprising at least:
an imaging device for transmitting an electrical signal corresponding to an area within said field of view:
a lens system/magnification functionality to magnify the imaged area;
a portable support system operatively connected to said imaging system and adapted to provide functional support to said imaging system, said portable support system comprising at least:
a power supply for supplying power to said imaging system
at least one controller for controlling said imaging system;
an image output device for outputting an image based on said electrical signal; and
a positioning system connected to said imaging system and adapted for moving said imaging system independently of said support system;
wherein said lens system/magnification functionality has optical characteristics and comprises at least one focus motor having feedback which provides focus data, and at least one zoom motor having feedback which provides magnification data;
wherein said image output device comprises a monitor for displaying the field of view; and
wherein said measurement system comprises:
an image overlay means for selecting a target object in the field of view displayed on said monitor, said image overlay means providing pixel data; and
calculating means for calculating the size of the target object, wherein the size of the target object is calculated by mathematically manipulating said optical characteristics, said focus data, said magnification data, and said pixel data.

17. The inspection system of claim 16, wherein said image overlay means includes cursor means to mark the target object in said video display means.

18. The inspection system of claim 16, wherein said calculating means includes an algorithm to calculate the size of the target object, said algorithm including the steps of multiplying said pixel data by said magnification data by a constant (K).

19. The inspection system of claim 18, wherein said constant is dependent upon said optical characteristics, said optical characteristics including a first value (V) equal to the percent distortion across an axis of said lens, a second value (FOV) equal to field of view of said lens, and a third value (OD) equal to a distance from said lens to the object.

20. A method of inspecting an area comprising:
providing an inspection device comprising at least:
an imaging system having an adjustable field of view and comprising at least an imaging device for transmitting an electrical signal corresponding to an area within said field of view, and a lens system having/ magnification functionality to magnify the imaged area said lens system/magnification functionality having a magnification ratio of no less than 50, and a waterproof enclosure containing said imaging device and said lens system;
a portable support system operatively connected to said imaging system and adapted to provide functional support to said imaging system, said portable support system comprising at least:
a power supply for supplying power to said imaging system
a controller for controlling said imaging system;
an image output device for outputting an image based on said electrical signal; and
an elongated member connected to said imaging system and adapted for moving said imaging system independently of said portable support system;
positioning said imaging system independently of said support system such that a target area is in said field of view while at a first magnification level;
imaging said target area at a second magnification level greater than the first magnification level; and
outputting an image of said target area.

21. The method of claim 20, wherein the step of outputting said digital image comprises:
encoding a computer-readable medium with said image.

22. The method of claim 21, wherein said digital image is transmitted via a world-wide network.

23. The method of claim 20, wherein the magnification ratio of said first and second magnification levels is no less than about 72:1.

24. A system of inspecting comprising:
an imaging system having an adjustable field of view and comprising at least:
an imaging device for transmitting an electrical signal corresponding to an area within said field of view:
a lens system /magnification functionality to magnify the imaged area;
a portable support system operatively connected to said imaging system and adapted to provide functional support to said imaging system, said portable support system comprising at least:
a power supply for supplying power to said imaging system
at least one controller for controlling said imaging system;
an image output device for outputting an image based on said electrical signal; and
a positioning system connected to said imaging system and adapted for moving said imaging system independently of said support system;
calculating the size of an object with said field of view by mathematically manipulating optical characteristics of a said lens system/magnification functionality, focus data from feedback of a focus motor of said imaging system, magnification data from feedback of a magnification motor of said imaging system, and pixel data of said object in the field of view displayed on a monitor.

25. A method of inspecting a pipe comprising:
extending an imaging system into a manhole;
imaging the interior of said manhole at a first magnification level;
locating a lateral pipe connected to said manhole; and
imaging the interior of said lateral pipe at a second magnification level greater than said first level.

* * * * *